United States Patent
Kurane

(10) Patent No.: US 8,026,956 B2
(45) Date of Patent: Sep. 27, 2011

(54) IMAGE SENSOR, IMAGE TAKING APPARATUS, AND STATE INSPECTION SYSTEM

(75) Inventor: Haruhisa Kurane, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 510 days.

(21) Appl. No.: 12/326,573

(22) Filed: Dec. 2, 2008

(65) Prior Publication Data

US 2009/0147120 A1    Jun. 11, 2009

(30) Foreign Application Priority Data

Dec. 7, 2007   (JP) ................................ 2007-316863

(51) Int. Cl.
*H04N 5/235* (2006.01)
*H04N 5/228* (2006.01)
*H04N 3/14* (2006.01)
*H04N 5/335* (2011.01)

(52) U.S. Cl. .................. 348/230.1; 348/222.1; 348/294

(58) Field of Classification Search ............... 348/222.1, 348/229.1, 230.1, 241, 294, 296–298, 302, 348/307–310, 362, 364–367, 311
See application file for complete search history.

(56) References Cited

U.S. PATENT DOCUMENTS

| | | | |
|---|---|---|---|
| 2004/0017339 A1* | 1/2004 | Wang | 345/87 |
| 2005/0206761 A1* | 9/2005 | Iguchi et al. | 348/294 |
| 2009/0147120 A1* | 6/2009 | Kurane | 348/311 |
| 2009/0153716 A1* | 6/2009 | Ota | 348/308 |

FOREIGN PATENT DOCUMENTS

| | | |
|---|---|---|
| JP | A-2-50582 | 2/1990 |
| JP | A-5-122614 | 5/1993 |
| JP | A-05-145857 | 6/1993 |
| JP | A-09-318547 | 12/1997 |
| JP | A-10-155112 | 6/1998 |
| JP | A-2005-062008 | 3/2005 |
| JP | A-2005-184411 | 7/2005 |
| JP | A-2007-174266 | 7/2007 |
| JP | A-2007-194687 | 8/2007 |
| JP | A-2007-221757 | 8/2007 |
| JP | A-2007-259428 | 10/2007 |
| JP | A-2007-281555 | 10/2007 |
| JP | A-2007-281556 | 10/2007 |
| JP | A-2007-288768 | 11/2007 |
| JP | A-2007-295525 | 11/2007 |

* cited by examiner

*Primary Examiner* — Ricky Mack
*Assistant Examiner* — Brandi Thomas
(74) *Attorney, Agent, or Firm* — Oliff & Berridge, PLC

(57) ABSTRACT

An image sensor includes: a photoelectric conversion unit including a plurality of photoelectric conversion elements, the photoelectric conversion elements being disposed in a two-dimensional matrix, the photoelectric conversion elements converting received light into electric charge and accumulating the electric charge; a reset processing unit for performing a reset process, the reset process being a process of removing electric charge accumulated in the photoelectric conversion elements of the photoelectric conversion unit in a first sub-frame period among the first to N-th sub-frame periods, the N being a natural number of two or more, the first to N-th sub-frame periods being obtained by dividing each frame period of a frame rate corresponding to a normal exposure time into an N number of periods in the first to N-th order; and a pixel signal readout unit for reading out a pixel signal in a non-destructive manner, the pixel signal being an electric signal corresponding to an amount of electrical charge accumulated in each of the photoelectric conversion elements in each of the first to N-th sub-frame periods.

8 Claims, 10 Drawing Sheets

IMAGE SENSOR, IMAGE TAKING APPARATUS, AND STATE INSPECTION SYSTEM

BACKGROUND

1. Technical Field

Several aspects of the present invention relate to an image sensor that is allowed to expose photoelectric conversion elements to light on a line-by-line basis. In particular, the invention relates to an image sensor and an image taking apparatus that are allowed to take an image at a frame rate corresponding to a normal exposure time and simultaneously take an image at a frame rate higher than the normal frame rate, and a state inspection system including the image taking apparatus.

2. Related Art

Due to problems such as increases in labor cost or from a humanitarian viewpoint of reductions in long-time simple work, a camera has been used in a manufacturing process or an inspection process. For example, by performing inspection using a camera or sorting out assembly parts using a camera, the shape of the subject is instantly measured and recognized. Simultaneously, the color or the like of the subject is also measured. For example, the shapes and colors of agricultural products, processed products thereof or the like are simultaneously inspected and these products are sorted based on the inspection result. Among inspection apparatuses using such a camera are agricultural product visual inspection apparatuses disclosed in JP-A-2005-62008 and JP-A-09-318547. These apparatuses measure both the shapes and colors of agricultural products using a charge coupled camera (CCD) camera and perform determination processes based on the measured shapes and colors. It is desired that these inspection apparatuses speed up for higher efficiency and the costs be reduced.

A CCD camera is typically used as an industrial camera for use in inspection apparatuses as described above. On the other hand, complementary metal oxide semiconductor (CMOS) cameras are also in widespread use mainly for entertainment and photography purposes. While CMOS cameras have become cheaper than CCD cameras and the image quality thereof has been improved, CCD cameras are still in the mainstream. This is partly because CCD cameras have a "global electronic shutter" function.

A CMOS sensor (CMOS image sensing element) typically performs exposure and reads out signals using a rolling shutter method in terms of the structure thereof. In the rolling shutter method, signals are read out from the lines (pixel lines) of the light reception area of the image sensor at different timings. Therefore, when an image of a moving subject is taken, the taken image is distorted. This phenomenon is remarkable when the subject is moving fast.

FIG. 6B is a drawing showing the timing of exposure of each line and the timing of readout of a pixel signal from each line in the related-art rolling shutter method. In FIG. 6A, the vertical axis represents the numbers of the lines included in the image sensor and the horizontal axis represents the time. For the sake of clarity, assume that there are eight lines, L1 to L8. In the rolling shutter method, while L1, L2, L3, . . . , L8 are sequentially scanned, readout and reset are performed on the scanned lines at timings indicated by arrows (↑) in FIG. 6B. Therefore, as shown in FIG. 6B, time lags occur among the exposure/readout timings of the lines. For example, a time lag corresponding to approximately one frame occurs between L1 and L8. When an image of a moving subject is taken, this time lag distorts the image. The distortion changes the shape of the subject in the image. This is a shortcoming in terms of shape recognition. A CCD camera also causes an image blur phenomenon when a subject moves. Accordingly, the shape recognition accuracy of the CCD camera also reduces depending on the moving speed or the like of the subject.

In order to take an image of a moving subject and recognize the shape of the subject while preventing occurrence of image distortion or image blurs, the frame rate must be increased. Unlike a CCD sensor, a CMOS sensor is allowed to increase the frame rate because a circuit can be mounted on the image sensor, the wiring is a high degree of freedom, and the like. For example, an image sensor having a high frame rate such as 180 fps has been developed for industrial application. In addition, there is a report that an image taken at a frame rate of 180 fps contains little waveform distortion. However, if the frame rate is increased, there occurs a problem that the exposure time is reduced, the output level of pixel signals is reduced, and thus the image quality (S/N) is reduced.

Hereafter, the amount of exposure will be described. A production facility or an inspection apparatus including an industrial camera adjusts the exposure amount by controlling both the exposure of the camera and the lighting environment, so as to improve the recognition accuracy. Specifically, the facility or apparatus optimally controls the aperture, the amount of illumination light, or the like so that an image of high quality is obtained at the frame rate of the camera (the rate corresponding to the normal exposure time is 30 fps), in other words, a sufficient signal level is outputted from an dark part of the subject and so that a bright part thereof is not saturated with signals (if there is a saturated part, the shape of the part will not be recognized). Therefore, such an industrial camera is significantly different from a camera for a photography purpose, which is expected to be used under various environments.

As a method for obtaining high image quality using a high frame rate (a frame rate N times higher than the normal frame rate), there are a method of making the illuminance of the lighting system N times higher and a method of making the pixel area of the image sensor N times larger for example. The former method is problematic in that it increases the running cost, that it is not environmentally friendly, and the like, while the latter method has a problem that it increases the cost of the camera.

Among methods for removing image distortion caused by a CMOS sensor is a method of providing a global shutter mechanism on an image sensor like in a CCD sensor. However, this method complicates the pixel structure, thereby disadvantageously reducing the pixel performance and increasing the cost of the image sensor.

Alternatively, there is a method of using two cameras and selectively using one of the two cameras as a high-speed camera for detecting the movement or shape of a subject and the other as a normal camera for detecting the color or texture of the subject, to obtain both high quality and high speed. However, this method has problems of high cost and high power consumption.

SUMMARY

An advantage of the invention is to provide an image sensor and an image taking apparatus that are allowed to take, at relatively low cost, a high-frame-rate image from which the shape or movement of a moving subject is accurately detected and an image from which the color or texture of the subject is accurately detected, and a state inspection apparatus including the image taking apparatus.

An image sensor according to a first aspect of the invention includes: a photoelectric conversion unit including a plurality of photoelectric conversion elements, the photoelectric conversion elements being disposed in a two-dimensional matrix, the photoelectric conversion elements converting received light into electric charge and accumulating the electric charge; a reset processing unit for performing a reset process, the reset process being a process of removing electric charge accumulated in each of the photoelectric conversion elements of the photoelectric conversion unit in a first sub-frame period among the first to N-th sub-frame periods, the N being a natural number of two or more, the first to N-th sub-frame periods being obtained by dividing each frame period of a frame rate corresponding to a normal exposure time into an N number of periods in the first to N-th order; and a pixel signal readout unit for reading out a pixel signal in a non-destructive manner, the pixel signal being an electric signal corresponding to an amount of electrical charge accumulated in each of the photoelectric conversion elements in each of the first to N-th sub-frame periods.

If this configuration is adopted, electric charge accumulated in each photoelectric conversion element is removed by performing a reset process in the first sub-frame period. After the reset process, a pixel signal corresponding to the amount of accumulated electric charge is successively read out in a non-destructive manner from each photoelectric conversion element by the pixel signal readout unit in each sub-frame period.

That is, a pixel signal is read out in a non-destructive manner in each of the first to N-th sub-frame periods. Therefore, there is obtained an advantage that pixel signal (a pixel signal corresponding to the normal exposure time) corresponding to the amount of electric charge accumulated through the first to N-th sub-frame periods in one frame corresponding to the normal exposure time and pixel signals (pixel signals corresponding to exposure times shorter than the normal exposure time) corresponding to the first to (N-1)-th sub-frame periods are obtained simultaneously.

For example, if an image of an subject moving fast is taken, the color or texture of the subject is accurately grasped from an image formed from a pixel signal corresponding to the normal exposure time and the shape or movement of the subject is accurately grasped from an image formed from a pixel signal corresponding to an exposure time shorter than the normal exposure time.

The above-mentioned "photoelectric conversion unit" is formed using the CMOS technology. Among image sensors using the CMOS technology is a VMIS (threshold voltage modulation image sensor).

The above-mentioned "(a pixel signal) is read out in a non-destructive manner" means that when electrical charge (pixel signal) is read out from a photoelectric conversion element, the electrical charge is read out without removing the electric charge accumulated in the photoelectric conversion element, that is, with the electrical charge held by the photoelectric conversion element. That is, since no reset process is performed on the photoelectric conversion element when the electric charge is read out therefrom, the electric charge corresponding to different exposure times may be read out again and again from the photoelectric conversion element accumulating the electric charge until a set exposure time is reached.

In the image sensor according to the first aspect of the invention, the pixel signal readout unit preferably reads out the pixel signal from each of the photoelectric conversion elements immediately after the reset process.

By adopting this configuration, a pixel signal is read out from a photoelectric conversion element whose accumulated electric charge has just been removed by performing a reset process. As a result, a pixel signal that has little accumulated electric charge is obtained. This pixel signal contains a fixed pattern noise component. Therefore, there is obtained an advantage that by obtaining a difference between this pixel signal and a pixel signal read out in each of the first to N-th sub-frame periods, a fixed pattern component is removed from each of the pixel signals read out in these sub-frame periods Among examples of the "fixed pattern noise" is dark current shading, which is a problem caused by long-time exposure, and noise caused by unevenness in threshold of pixels or differences in sensitivity among the sensors.

An image taking apparatus according to a second aspect of the invention includes the image sensor according to claim 1. In this case, the image taking apparatus has a function of controlling an amount of exposure of each of the photoelectric conversion elements of the image sensor, and the amount of exposure of each of the photoelectric conversion elements is controlled so that a pixel signal corresponding to an amount of electric charge accumulated during the normal exposure time, the pixel signal being read out by the pixel signal readout unit immediately before the reset process does not reach a saturation level.

By adopting this configuration, the exposure amount is controlled so that the level of a pixel signal corresponding to the amount of electric charge accumulated during the normal exposure time does not reach the saturation level. Therefore, "white flying" or the like does not occur in an image corresponding to the normal exposure time. As a result, there is obtained an advantage that all the sub-frames become unsaturated and thus an image, from which the texture, movement, or the like of a subject is more accurately detected, is obtained. Among methods for controlling the exposure amount are an aperture control method and an illumination light amount control method.

An image taking apparatus according to a third aspect of the invention includes: the image sensor according to claim 1; a quickly-taken-image data generation unit for generating quickly-taken-image data corresponding to each of the first to N-th sub-frame periods on the basis of a pixel signal corresponding to an amount of electric charge accumulated during the first to N-th sub-frame periods, the pixel signal being read out by the pixel signal readout unit of the image sensor; and a normally-taken-image data generation unit for generating normally-taken-image data, the normally-taken-image data being image data corresponding to the normal exposure time, on the basis of pixel signal data corresponding to an amount of electric charge accumulated during the first sub-frame period and a pixel signal corresponding to an amount of electric charge accumulated during each of the first to N-th sub-frame periods, the pixel signal data and the pixel signal both being read out by the pixel signal readout unit of the image sensor. In this case, image taking apparatus has a function of controlling an amount of exposure of each of the photoelectric conversion elements of the image sensor.

By adopting this configuration, generating quickly-taken-image data corresponding to each of the first to N-th sub-frame periods are generated on the basis of pixel signals obtained by the image sensor according to the first aspect of the invention and corresponding to the amounts of electric charge accumulated during each of the first to N-th sub-frame periods. Also, normally-taken-image data is generated on the basis of pixel signal data corresponding to the amount of electric charge accumulated during the first sub-frame period and a pixel signal corresponding to the amount of electric charge accumulated through the first to N-th sub-frame periods.

As a result, an advantage similar to that of the image sensor according to the first aspect of the invention is obtained. Also, normally-taken-image data obtained from an image of a subject taken at the normal frame rate and quickly-taken-image data obtained from an image of the subject taken at a frame rate higher than the normal frame rate is simultaneously generated. As a result, there is obtained an advantage that, for example, when this image taking apparatus is applied to a system for inspecting the state (appearance) of a product moving while riding on a conveyor belt or the like, the color or texture of the subject (product) is detected from the normally-taken-image data and the shape or movement of the subject is detected from the quickly-taken-image data so that a highly accurate inspection is performed.

In the image taking apparatus according to the third aspect of the invention, the pixel signal readout unit preferably reads out a pixel signal from each of the photoelectric conversion elements immediately after a reset process, the quickly-taken-image data generation unit generates the quickly-taken-image data corresponding to each of the first to N-th sub-frame periods on the basis of a difference value between a luminance value of a first pixel signal and any one of a luminance value of a second pixel signal and a luminance value of a third pixel signal, the first pixel signal corresponding to an amount of electric charge accumulated during an n-th sub-frame period from the first sub-frame period, the n being a natural number of two or more and N or less, the second pixel signal corresponding to an amount of electric charge accumulated during an (n-1)-th sub-frame period from the first sub-frame period, the third pixel signal being read out immediately after the reset process, the first to third pixel signals being read out by the pixel signal readout unit, and the normally-taken-image data generation unit preferably generates the normally-taken-image data on the basis of a difference value between a luminance value of a fourth pixel signal and a luminance value of a fifth pixel signal, the fourth pixel signal corresponding to an amount of electric charge accumulated during the first sub-frame period, the fifth pixel signal corresponding to an amount of electric charge accumulated during the first to N-th sub-frame periods, the fourth and fifth pixel signals being read out by the pixel signal readout unit.

By adopting this configuration, a fixed pattern component is removed from the quickly-taken-image data and normally-taken-image data. As a result, there is obtained an advantage that the quality of these pieces of image data is improved.

In the image taking apparatus according to the third aspect of the invention, an amount of exposure of each of the photoelectric conversion elements is preferably controlled so that a pixel signal corresponding to an amount of electric charge accumulated during the normal exposure time, the pixel signal being read out by the pixel signal readout unit immediately before the reset process, does not reach a saturation level.

By adopting this configuration, the exposure amount is controlled so that the level of a pixel signal corresponding to the amount of electric charge accumulated during the normal exposure time does not reach the saturation level. Therefore, white flying or the like does not occur in an image corresponding to the normal exposure time. As a result, there is obtained an advantage that all the sub-frames become unsaturated and thus an image, from which the texture, movement, or the like of a subject is more accurately detected, is obtained. Among methods for controlling the exposure amount are an aperture control method and an illumination light amount control method.

A state inspection system for inspecting a state of an inspection subject moving in an inspection area according to a fourth aspect of the invention includes: the image taking apparatus according to claim 4; a lighting system for lighting the inspection subject; a light amount control unit for controlling a light amount of the lighting system on the basis of normally-taken-image data obtained by taking an image of the inspection subject using the image taking apparatus; a first detection unit for detecting information related to a texture of the inspection subject on the basis of the normally-taken-image data; and a second detection unit for detecting information related to any one of a shape and a movement of the inspection subject on the basis of the quickly-taken-image data.

By adopting this configuration, for example, in the initialization process, an image of an inspection subject is taken using the image taking apparatus according to the third aspect of the invention. After normally-taken-image data is generated, the light amount of the lighting system that is lighting the inspection subject is controlled by the light amount control unit on the basis of this normally-taken-image data. After the light amount is properly controlled in this way, the inspection process is started. Images of the inspection subject moving in the inspection area are taken by the image taking apparatus according to the third aspect of the invention so that quickly-taken-image data and normally-taken-image data is generated. After these pieces of image data are generated, the texture of the inspection subject, such as color, is detected by the first detection unit on the basis of the normally-taken-image data and the shape, movement, or the like of the inspection subject is detected by the second detection unit on the basis of the quickly-taken-image data.

That is, the texture of the moving inspection subject, such as color, is detected from the normally-taken-image obtained at the normal frame rate and the shape or movement thereof is detected from the quickly-taken-image data obtained at a frame rate higher than the normal frame rate. As a result, there is obtained an advantage that the inspection accuracy indicating whether an abnormality is included in the texture, shape, or the like of the inspection subject is made higher than that in a case where an inspection is performed using only any one of an image taken at the normal frame rate and an image taken at a higher frame rate. Also, since the amount of illumination light emitted by the lighting system is optimized, there is obtained an advantage that the inspection accuracy is further improved.

The state inspection system according to the fourth aspect of the invention preferably further includes a histogram creation unit for creating a histogram of luminance information on the basis of the normally-taken-image data obtained by taking an image of the inspection subject using the image taking apparatus. In this case, the light amount control unit preferably controls the light amount of the lighting system on the basis of the histogram created by the histogram creation unit.

By adopting this configuration, an image of an inspection subject is taken using the image taking apparatus according to the third aspect of the invention in the initialization process. After normally-taken-image data is generated, a histogram of luminance information is created on the basis of this normally-taken-image data by the histogram creation unit. After the histogram is created, the amount of light emitted by the lighting system is controlled by the light amount control unit so that the histogram becomes an ideal one. Thus, the normally-taken-image data of more appropriate quality is obtained. As a result, there is obtained an advantage that the inspection accuracy is further improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
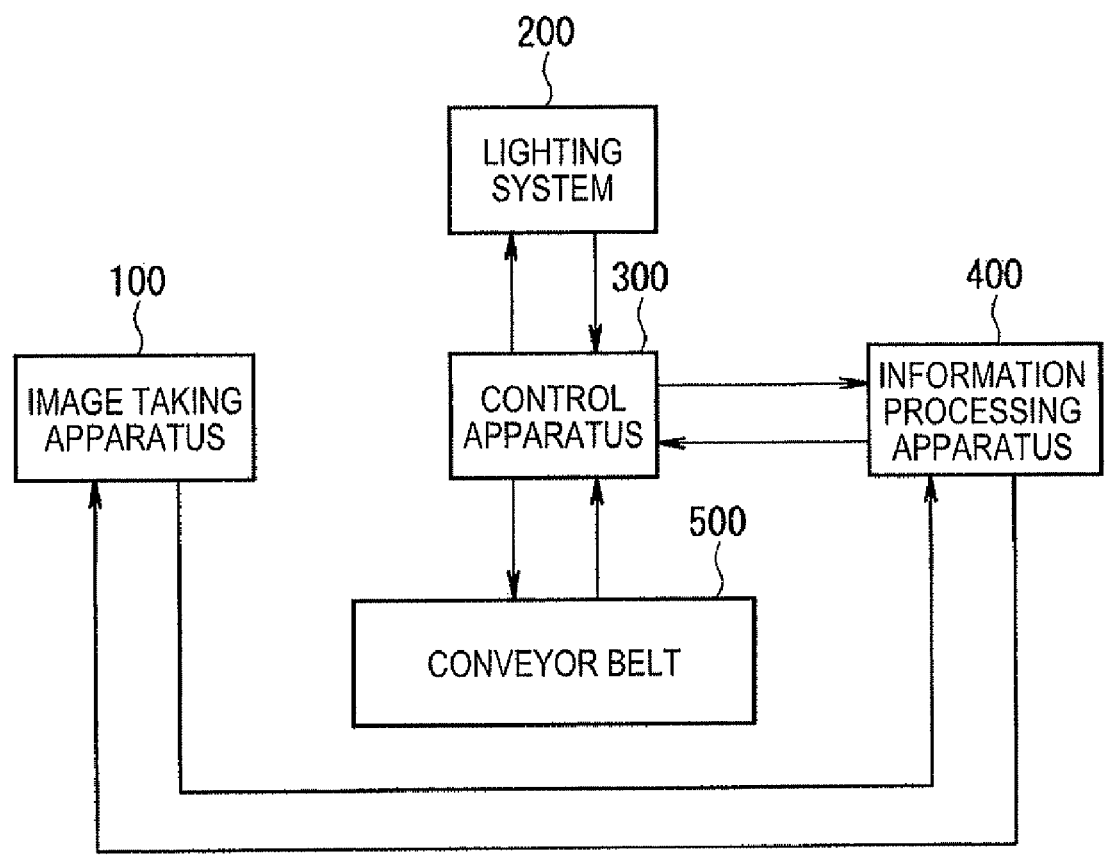
FIG. 1 is a block diagram showing a schematic configuration of a state inspection system 1 according to an embodiment of the invention.

Now, an image sensor, an image taking apparatus, and an image taking system according to an embodiment of the invention will be described with reference to the accompanying drawings. First, referring to FIG. 1, a state inspection system 1 according to this embodiment will be described. FIG. 1 is a block diagram showing a schematic configuration of the state inspection system 1 according to this embodiment.

As shown in FIG. 1, the state inspection system 1 includes an image taking apparatus 100 that is allowed to take images in frames each corresponding to the normal exposure time, that is, to take images at the normal frame rate and at the same time to take images in first to N-th (N is a natural number of two or more) sub-frames obtained by dividing one frame into N periods, that is, to take images at a frame rate N times higher than the normal frame rate, a lighting system 200 for lighting an inspection subject, a control apparatus 300 for controlling operations of the lighting system 200 and a conveyor belt 500, an information processing apparatus 400 for controlling operations of the image taking apparatus 100, and the conveyor belt 500 for conveying an inspection subject.

The image taking apparatus 100 and information processing apparatus 400 are coupled to each other so that these apparatuses exchange data with each other via a data transmission path. Also, the lighting system 200, information processing apparatus 400 and conveyor belt 500 are coupled to one another so that these apparatuses exchange data with the control apparatus 300 via data transmission paths.

The image taking apparatus 100 has a function of reading out pixel signals at a frame rate N times higher than the normal frame rate, that is, it performs a pixel signal readout process on an identical subject N times in one normal frame period. Therefore, the image taking apparatus 100 generates image data corresponding to the normal exposure time (hereafter referred to as "normally-taken-image data") and image data corresponding to readout quickly performed n times (hereafter referred to as "quickly-taken-image data").

The lighting system 200 is disposed above the conveyor belt 500 and lights an inspection subject placed on the belt of the conveyor belt 500. Also, the lighting system 200 changes the amount of illumination light in accordance with a control command from the control apparatus 300.

The control apparatus 300 controls operations of the lighting system 200 and conveyor belt 500 in accordance with a command from the information processing apparatus 400, for example, it controls the amount of illumination light emitted by the lighting system 200, the start or end of an operation of the conveyor belt 500, the speed of the belt (transportation speed), and the like.

The information processing apparatus 400 centrally controls operations of the state inspection system 1 on the basis of normally-taken-image data and quickly-taken-image data obtained from images of an inspection subject taken by the image taking apparatus 100. For example, the information processing apparatus 400 generates a command for controlling the amount of illumination light emitted by the lighting system 200 or a command for controlling an operation of the conveyor belt 500 or detects the state of an inspection subject.

Specifically, when controlling the amount of illumination light during an initialization operation of the system, the information processing apparatus 400 creates a histogram of luminance information on the basis of the normally-taken-image data obtained from an image of an inspection subject taken by the image taking apparatus 100 and generates a command for controlling the amount of illumination light emitted by the lighting system 200 so that the histogram is a histogram indicating a proper luminance distribution.

Also, when performing a process for detecting the state of an inspection subject, the information processing apparatus 400 detects the color, texture, or the like of the inspection subject on the basis of normally-taken-image data, as well as detects the shape of the inspection subject on the basis of quickly-taken-image data.

For example, if an image from which the color or texture, or shape of the inspection subject is correctly detected is not obtained by only controlling the amount of illumination light emitted by the lighting system 200, the information processing apparatus 400 generates a command for controlling the speed of the belt of the conveyor belt 500 on the basis of the normally-taken-image data and quickly-taken-image data. For example, if a proper image is not obtained due to too high a transportation speed, the information processing apparatus 400 generates a command for reducing the speed of the belt.

The information processing apparatus 400 transmits a command generated as described above to the control apparatus 300. Then, the control apparatus 300 controls an operation of the lighting system 200 or conveyor belt 500 in accordance with the command.

The information processing apparatus 400 includes a computer system for realizing the above-mentioned functions using software and executing software for controlling hardware necessary to realize the above-mentioned functions. Although the hardware configuration thereof is not shown, the computer system includes CPU (central processing unit), a RAM (random access memory), and a ROM (read only memory), which are coupled to one another via various internal and/or external buses such as a PCI (peripheral component interconnect) bus.

Coupled to these buses via input/output interfaces (I/F) such as an IEEE1394, a USB, and a parallel port are a storage unit such as an HDD (hard disk drive), a display such as a CRT or an LCD monitor, input devices such as an operation panel, a mouse, and a keyboard, a network card for communicating with external devices on a network (data transmission path), and the like.

When the information processing apparatus 400 is powered on, a system program such as BIOS stored in the ROM or the like loads, into the RAM, various dedicated computer programs for realizing the functions of the above-mentioned components previously stored in the HDD or the like. Then, the CPU performs predetermined control and calculation processes using various resources in accordance with commands written in the loaded programs. In this way, the above-mentioned functions are realized on software.

The conveyor belt 500 is made of a black material of low reflectivity so that illumination light emitted from the lighting system 200 is hard to be reflected by the conveyor belt 500. Also, the conveyor belt 500 starts or stops an operation thereof or changes the speed of the belt in accordance with a control command from the control apparatus 300.

Figure 2:
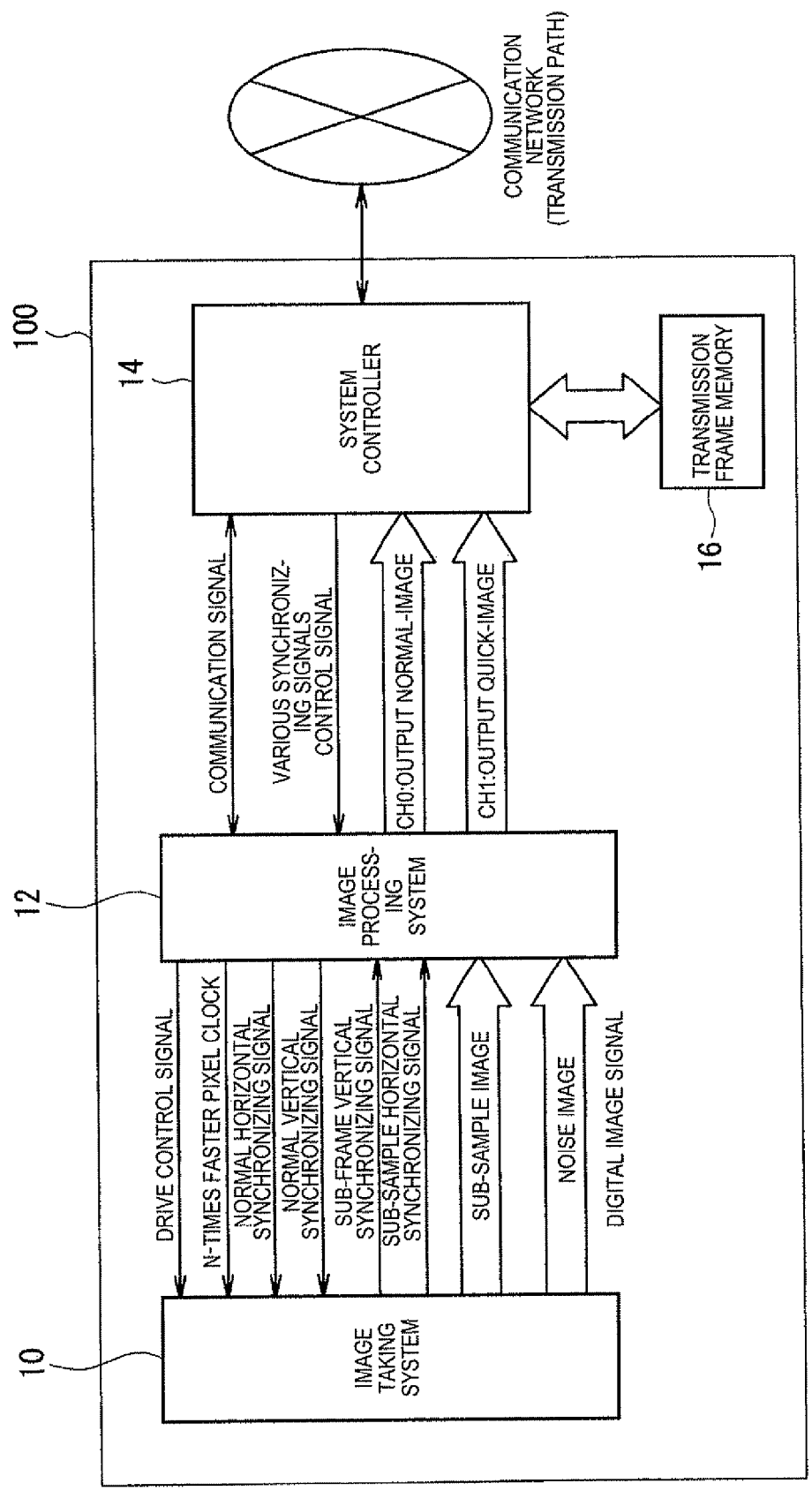
FIG. 2 is a block diagram showing an internal configuration of an image taking apparatus 100.

Next, referring to FIG. 2, an internal configuration of the image taking apparatus 100 will be described. FIG. 2 is a block diagram showing an internal configuration of the image taking apparatus 100.

As shown in FIG. 2, the image taking apparatus 100 includes an image taking system 10 including a CMOS sensor cell array (image sensor), an image processing system 12 for generating image data on the basis of pixel signals read out from the sensor cell array, a system controller 14 for transmitting image data generated in the image processing system 12 or controlling an operation of the image taking system 10 or image processing system 12 in accordance with a command from the information processing apparatus 400, and a transmission frame memory 16 used when performing a process for transmitting image data.

Figure 3:
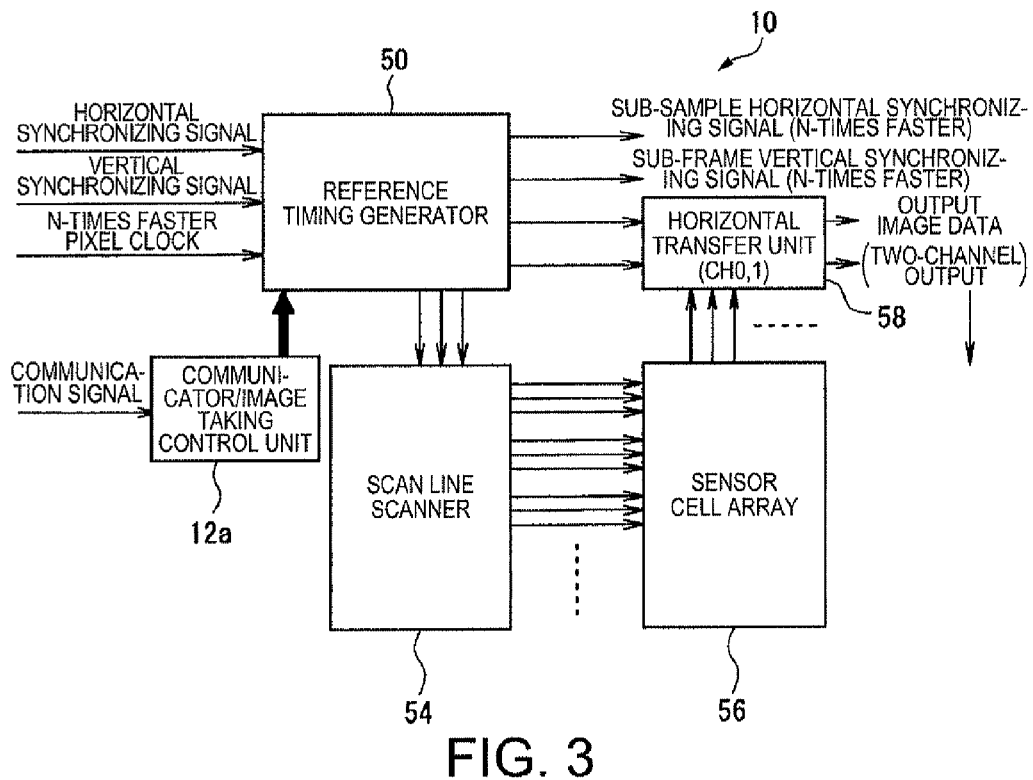
FIG. 3 is a block diagram showing an internal configuration of an image taking system 10.
Figure 4:
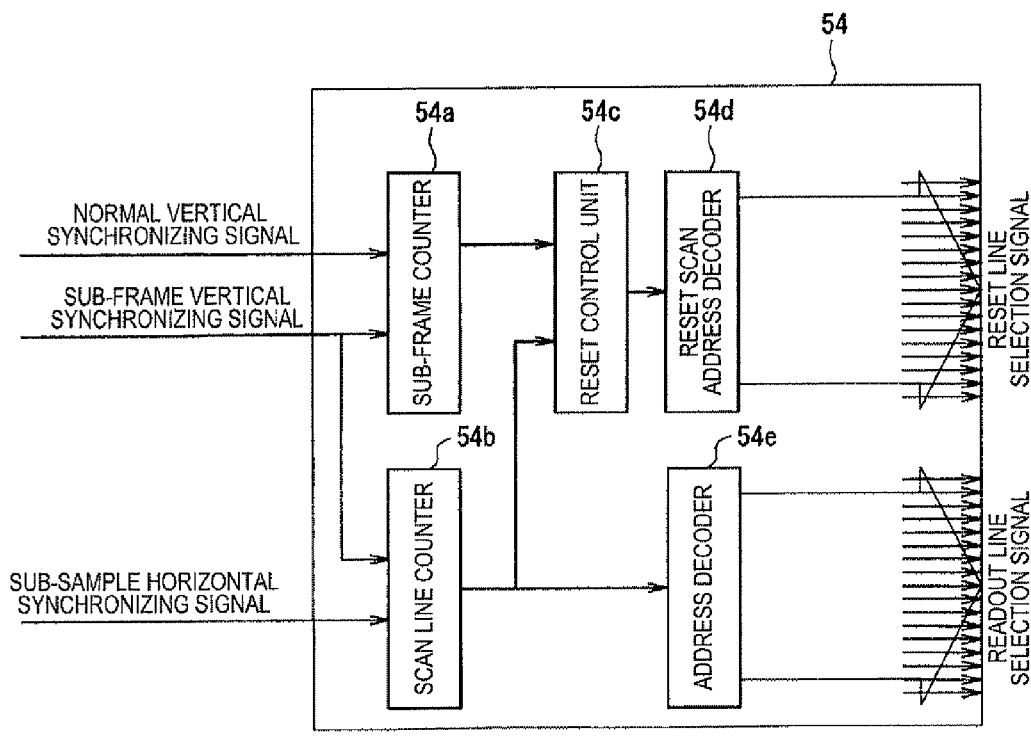
FIG. 4 is a block diagram showing an internal configuration of a scan line scanner 54.

Next, referring to FIGS. 3 and 4, an internal configuration of the image taking system 10 will be described. FIG. 3 is a block diagram showing an internal configuration of the image taking system 10 and FIG. 4 is a block diagram showing an internal configuration of a scan line scanner 54.

As shown in FIG. 3, the image taking system 10 includes a reference timing generator 50, the scan line scanner 54, a sensor cell array 56, and a horizontal transfer unit 58.

The reference timing generator 50 generates a sub-sample horizontal synchronizing signal that is a horizontal synchronizing signal having a speed N times higher (a frequency N times higher than the normal frequency) than that of the normal horizontal synchronizing signal and a sub-frame vertical synchronizing signal that is a vertical synchronizing signal having a speed N times higher (a frequency N times higher than the normal frequency) than that of a normal vertical synchronizing signal on the basis of a pixel clock having a speed N times higher (hereafter referred to as "N times faster pixel clock") than that of a normal pixel clock, a normal horizontal synchronizing signal, and a vertical synchronizing signal received from the image processing system 12. Then, the reference timing generator 50 outputs the generated synchronizing signals to each of the scan line scanner 54 and horizontal transfer unit 58.

Here, pixel signal readout operations performed in a non-destructive manner N times at a N times higher speed (if the normal rate is 30 fps, n×30 fps) in one normal frame period (e.g., the frame rate is 30 fps) are referred to as "sub-sampling." Also, an N number of periods in each of which sampling is performed are referred to as "first to N-th sub-frames."

The scan line scanner 54 generates a reset line selection signal for enabling a line to be subjected to a reset process, on the basis of various signals from the reference timing generator 50 and image processing system 12. Then, the scan line scanner 54 outputs the generated reset line selection signal to the sensor cell array 56.

Also, the scan line scanner 54 successively generates a readout line selection signal for enabling a line from which a pixel signal is to be read out. Then, the scan line scanner 54 successively outputs the generated readout line selection signal to the sensor cell array 56.

The sensor cell array 56 includes a light reception area in which multiple sensor cells (pixels) formed using the CMOS technology and each including a light reception element (photodiode, etc.) and an amplifier are disposed in a two-dimensional matrix. In the sensor cell array 56, a common address line, a common reset line, and a common readout line are coupled to lines each including pixels (lines orthogonal to the scan direction in this embodiment).

Various drive signals (selection signals) are transmitted to sensor cells included in each line via the above-mentioned three control lines. When the address line and readout line are enabled, accumulated electric charge (pixel signals) are transferred (outputted) to the horizontal transfer unit 58 via a signal line.

The image taking system 10 includes an image taking lens (not shown). Using the image taking lens, the image taking system 10 collects light from a subject on the sensor cell array 56, and then accumulates electrical charge corresponding to the amount of the collected light on the pixels of the sensor cell array 56.

By adopting this configuration, the sensor cell array 56 enables (selects) a line including pixels to be subjected to a reset operation or a readout operation via the address line on the basis of a selection signal provided by the scan line scanner 54. If pixels included in the line selected using the selection signal are subjected to a reset operation, a signal for instructing a reset operation is inputted into the pixels via the reset line. In contrast, if pixel signals are read out from such pixels, a signal for instructing transfer of accumulated electric charge is inputted into the pixels via the readout line. In this case, the sensor cell array 56 is allowed to transfer the pixel signals without destroying the electric charge (pixel signals) accumulated on the pixels, that is, with the electric charge held by the pixel signals. In other words, the sensor cell array 56 is allowed to read out the pixel signals in a non-destructive manner.

As described above, if a signal for instructing a reset operation is inputted into the pixels selected by the selection signal, a reset operation is performed; if a signal for instructing transfer of accumulated electric charge is inputted, the accumulated electric charge is transferred in a non-destructive manner to the horizontal transfer unit 58 via a signal line.

The horizontal transfer unit 58 has two channels for transferring pixel data for noise removal and other pixel data independently. The horizontal transfer unit 58 A/D-converts pieces of data indicating N types of pixel signals (analog signals) (hereafter referred to as "pixel signal data") corresponding to different exposure times read out from the pixels of the sensor cell array 56 and successively outputs the resultant pieces of digital data (hereafter referred to as "pixel data") to the image processing system 12 in serial. The detailed configuration will be described later.

Next, referring to FIG. 4, an internal configuration of the scanning line scanner 54 will be described.

As shown in FIG. 4, the scan line scanner 54 includes a sub-frame counter 54a, a scan line counter 54b, a reset control unit 54c, a reset scan address decoder 54d, and an address decoder 54e.

The sub-frame counter 54a repeatedly performs a counting-up operation on the basis of a normal vertical synchronizing signal and a sub-frame vertical synchronizing signal from the reference timing generator 50 and outputs the counted value to the reset control unit 54c. Specifically, the sub-frame counter 54a resets the counted value in synchronization with a normal vertical synchronizing signal and counts up the sub-frame number in synchronization with a sub-frame vertical synchronizing signal.

The scan line counter 54b repeatedly performs a counting-up operation on the basis of a sub-frame vertical synchronizing signal and a sub-sample horizontal synchronizing signal from the reference timing generator 50 and outputs the counted value to each of the reset control unit 54c and address decoder 54e. Specifically, the scan line counter 54b resets the counted value in synchronization with a sub-frame vertical synchronizing signal and counts up the line number in synchronization with a sub-sample horizontal synchronizing signal.

The value counted by the scan line counter 54b corresponds to the number of a line including pixels in the sensor cell array 56.

The reset control unit 54c outputs the value counted by the scan line counter 54b to the reset scan address decoder 54d only when the value counted by the sub-frame counter 54a is the initial value (e.g., "1"). Otherwise, the reset control unit 54c outputs a value (e.g., "0") indicating that there is no selected line) to the reset scan address decoder 54d. Specifically, when the value counted by the sub-frame counter 54a is a value corresponding to the first sub-frame period, the reset control unit 54c outputs the value counted by the scan line counter 54b to the reset scan address decoder 54d.

On the basis of the counted value inputted from the reset control unit 54c, the reset scan address decoder 54d generates a reset line selection signal for selecting and enabling a line having a line number corresponding to the counted value as a "reset line" and outputs the generated signal to the sensor cell array 56. Thus, only the selected line is enabled and other lines are disabled.

On the basis of the value counted by the scan line counter 54b, the address decoder 54e generates a readout line selection signal for selecting and enabling a line having a line number corresponding to the counted value as a "readout line" and outputs the generated signal to the sensor cell array 56. Thus, only the selected line is enabled and other lines are disabled.

Next, referring to FIGS. 5 and 6A and 6B, a method for reading out pixel signals from the sensor cell array 56 of the image taking system 10 will be described in more detail.

Figure 5:
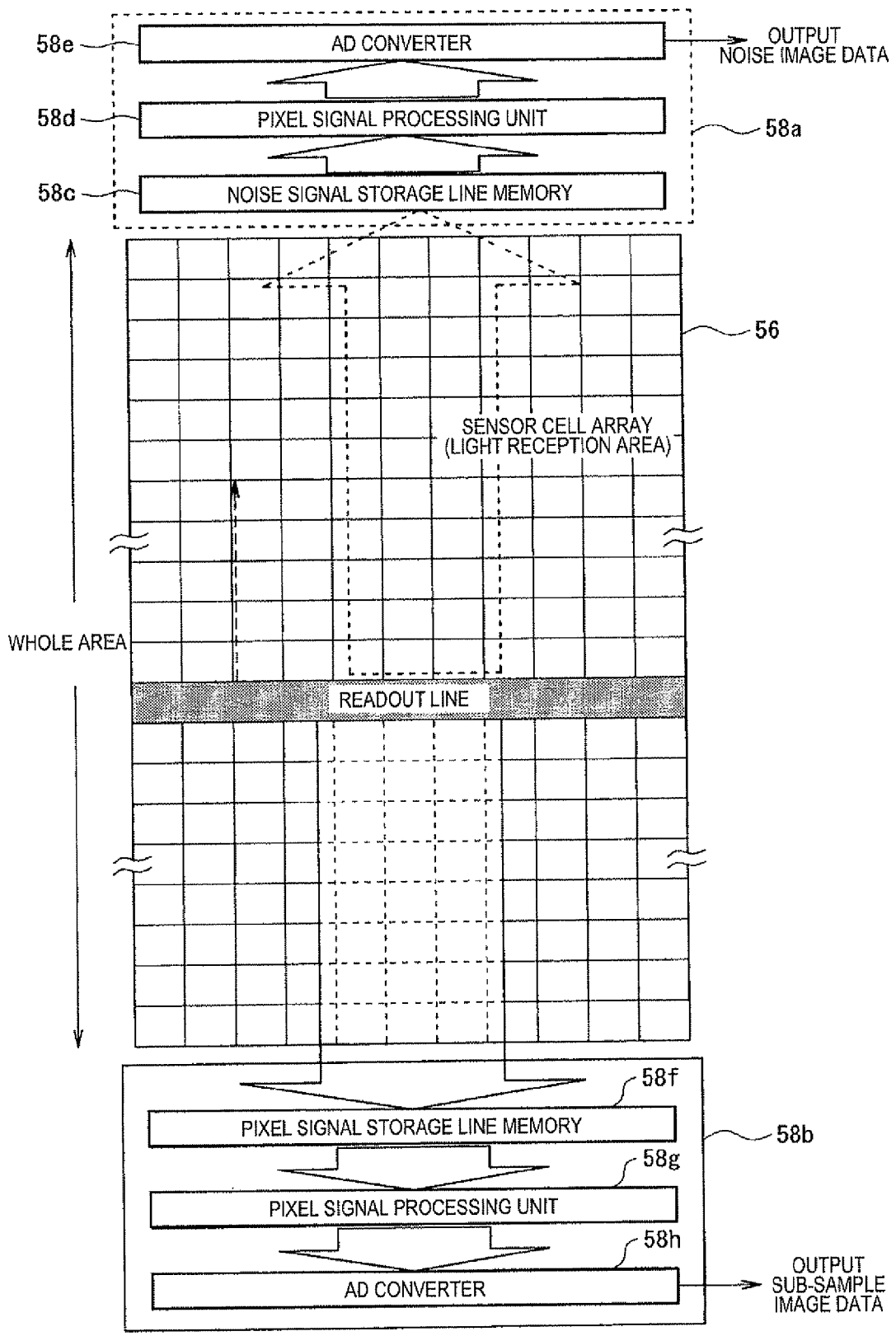
FIG. 5 is a drawing showing an example of the timing at which pixel signals are read out from each line and a detailed configuration of a horizontal transfer unit 58.

FIG. 5 is a drawing showing an example of the timing at which pixel signals are readout from each line and a detailed configuration of the horizontal transfer unit 58. FIG. 6A is a drawing showing the timing at which pixel signals are read out from each line in each sub-frame using an exposure/readout method according to this embodiment and FIG. 6B is a drawing showing the timing at which pixel signals are read out from each line using the related-art exposure/readout method. First, referring to FIG. 5, a detailed configuration of the horizontal transfer unit 58 will be described.

As shown in FIG. 5, the horizontal transfer unit 58 includes a noise horizontal transfer unit 58a (CH0) and a pixel signal horizontal transfer unit 58b (CH1).

The noise horizontal transfer unit 58a includes a noise signal storage line memory 58c for storing pixel signal data read out from each pixel immediately after a reset process on a line-by-line basis, a pixel signal processing unit 58d for performing a pixel signal process such as signal level adjustment on the pixel signal data stored in the noise signal storage line memory 58c on a line-by-line basis, and an A/D converter 58e for A/D-converting the resultant pixel signal data.

The pixel signal horizontal transfer unit 58b includes a pixel signal storage line memory 58f for storing pixel signal data read out from each pixel in each of the first to N-th sub-frames and corresponding to the amount of accumulated electric charge, a pixel signal processing unit 58g for performing a pixel signal process such as signal level adjustment on the pixel signal data stored in the pixel signal storage line memory 58f, and an AD converter 58h for A/D-converting the resultant pixel signal data.

Next, a reset process and a pixel signal readout process performed in each sub-frame period will be described.

First, in the first sub-frame period, a readout line selection signal is sequentially inputted from the scan line scanner 54 and, as shown in FIG. 5, a line corresponding to this selection signal is enabled as a readout line one after another. Then, a pixel signal corresponding to the normal exposure time in the preceding frame is read out in a non-destructive manner from the enabled line. Immediately after this readout, lines corresponding to reset line selection signals successively inputted from the scan line scanner 54 are successively enabled as reset lines. Then, the enabled lines are subjected to reset processes.

Also, in this embodiment, pixel signals (noise signals) are read out from pixels in each line immediately after subjected to the reset process. Such pixel signals are signals in most of which fixed pattern noise components are dominant, since these signals have hardly been exposed to light.

In the first sub-frame period, pixel signal data read out from each readout line and corresponding to the normal exposure time is converted into digital pixel data in the pixel signal horizontal transfer unit 58b and the resultant digital pixel data is transferred to the image processing system 12.

On the other hand, pixel signal data read out from each line immediately after a reset process is converted into digital pixel data in the noise horizontal transfer unit 58a and the resultant digital pixel data is transferred to the image processing system 12.

Subsequently, in the second to N-th sub-frame periods, readout line selection signals are successively inputted from the scan line scanner 54 and lines corresponding to these selection signals are successively enabled as readout lines. Pixel signals are successively read out in a non-destructive manner from the enabled lines.

The pixel signal data read out from each readout line in each of the second to N-th sub-frame periods is converted into digital pixel data in the pixel signal horizontal transfer unit 58b and the resultant digital pixel data is transferred to the image processing system 12. Here, pixel data read out from each line immediately after a reset process is referred to as "noise image data" and pixel data read out from each line in each of the first to N-th sub-frame periods is referred to as "first to N-th sub-sample image data".

Next, referring to FIG. 6A, pixel signal readout timings and image data output timings in each sub-frame period will be described using a specific example. In an example shown in FIG. 6A, it is assumed that the number N of times higher than the normal frame rate is four and the number of lines is eight (L1 to L8 in FIG. 6A correspond to the eight lines).

Figure 6:
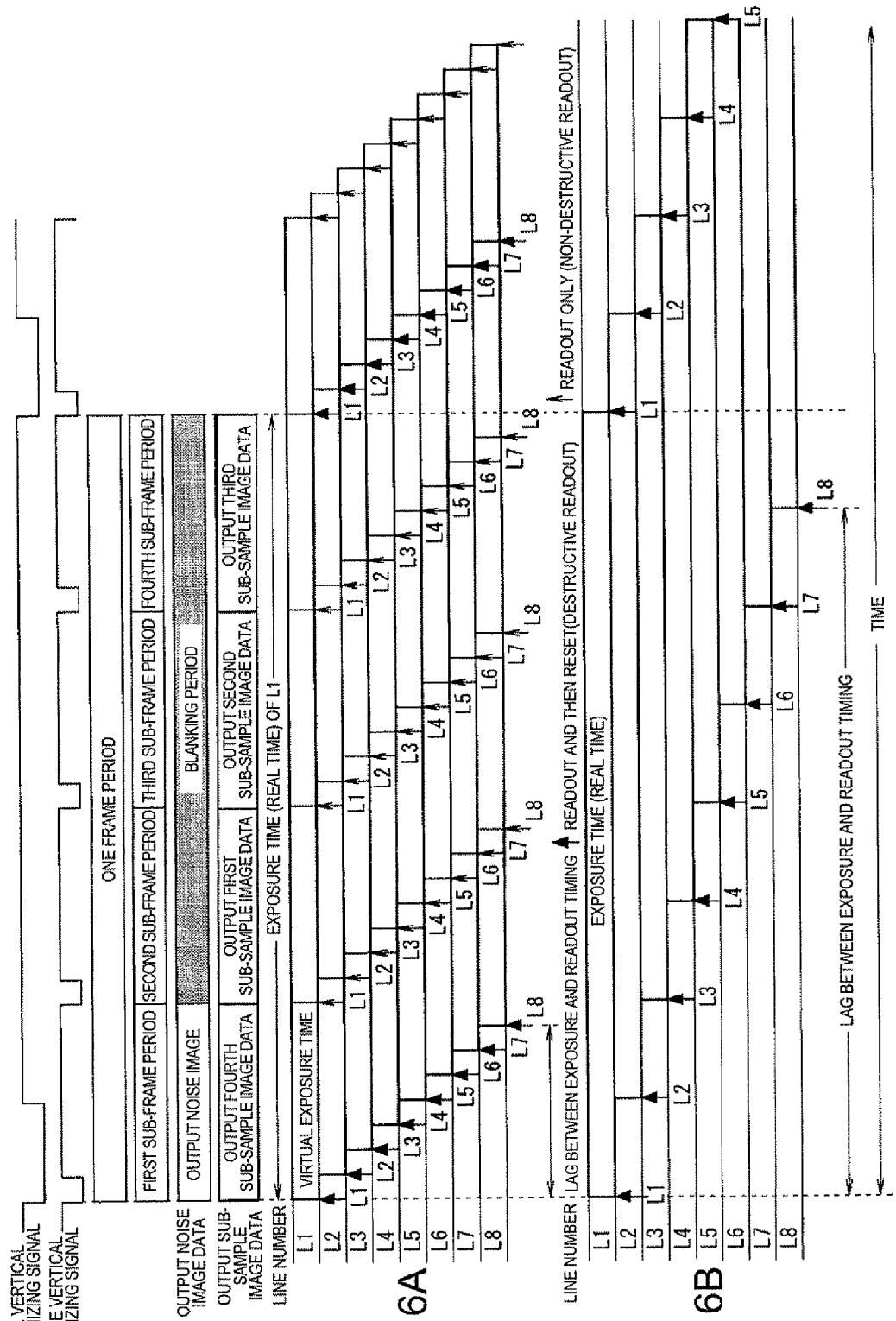
FIG. 6A is a drawing showing the timing at which pixel signals are read out from each line using an exposure/readout method according to this embodiment.
FIG. 6B is a drawing showing the timing at which pixel signals are read out from each line using an exposure/readout method according to a related-art example.

As shown in FIG. 6A, a normal frame period starts in synchronization with a normal vertical synchronizing signal and, at the same time, the first sub-frame period starts. At the start timing of the first sub-frame period, that is, at the end timing of the fourth sub-frame period, pixel signals corresponding to the normal exposure time in the preceding frame are read out in a non-destructive manner and, immediately after, reset processes are performed. Therefore, during the first sub-frame period, pixel signal data corresponding to the normal exposure time in the preceding frame is converted into digital data by the pixel signal horizontal transfer unit 58b and the resultant digital data is outputted as the fourth sub-sample image data to the image processing system 12.

Also, the lines from each of which a pixel signal corresponding to the preceding frame has been read out are successively subjected to reset processes. Then, pixel signals are successively read out from pixels included in the lines immediately after subjected to the reset processes. Such pixel signals are converted into digital data by the noise horizontal transfer unit 58a and the resultant digital data is outputted as noise image data to the image processing system 12.

On the other hand, after the reset processes are performed, pixel signals corresponding to the amounts of accumulated electric charge are successively read out from each line in a non-destructive manner during a period (virtual exposure period) from the falling edge of a sub-frame vertical synchronizing signal in the first sub-frame (hereafter referred to as a "first sub-frame vertical synchronizing signal") to the falling edge of a second sub-frame vertical synchronizing signal. Specifically, such pixel signals are read out at the start timing of the second sub-frame period. These pieces of pixel signal data are converted into digital data by the pixel signal horizontal transfer unit 58b and the resultant digital data is outputted as first sub-sample image data to the image processing system 12.

When the second sub-frame period starts, pixel signals corresponding to the amounts of accumulated electric charge are successively read out from each line in a non-destructive manner during a period from the falling edge of the second sub-frame vertical synchronizing signal to the falling edge of a third sub-frame vertical synchronizing signal. Specifically, such pixel signals are read out at the start timing of the third sub-frame period. These pieces of pixel signal data are converted into digital data by the pixel signal horizontal transfer unit 58b and the resultant digital data is outputted as second sub-sample image data to the image processing system 12.

Like in the second sub-frame period, when the third sub-frame period starts, pixel signals corresponding to the amounts of accumulated electric charge are read out from each line during a period from the falling edge of the third sub-frame vertical synchronizing signal to the falling edge of a fourth sub-frame vertical synchronizing signal, specifically, at the start timing of the fourth sub-frame period. These pieces of pixel signal data are converted into digital data by the pixel signal horizontal transfer unit 58b and the resultant digital data is outputted as third sub-sample image data to the image processing system 12.

When the fourth sub-frame period starts, pixel signals corresponding to the amounts of accumulated electric charge are read out from each line during a period from the falling edge of the fourth sub-frame vertical synchronizing signal to the falling edge of a first sub-frame vertical synchronizing signal in a subsequent frame, specifically, at the start timing of the first sub-frame of the subsequent frame. These pieces of pixel signal data are converted into digital data by the pixel signal horizontal transfer unit 58b and the resultant digital data is outputted as the fourth sub-sample image data to the image processing system 12.

As such, reset processes, noise image data readout processes, and first to fourth sub-sample image data readout processes will be sequentially performed.

In this way, a pixel signal readout process is performed four times at a frame rate four times higher than the normal frame rate in one normal frame period. As a result, a time lag between the exposure and each readout timing in each sub-frame period is one-fourth that in the related-art method shown in FIG. 6B. That is, if pixel signals are read out at a frame rate N times higher than the normal frame rate, the time lag becomes one-N-th.

Also, since pixel signals are read out in a non-destructive manner, pixel signals corresponding to four amounts of accumulated electric charge (exposure time) corresponding to readout timings are read out. In the example shown FIG. 6A, pixel signals corresponding to four exposure times included in the normal exposure time are read out.

Figure 7:
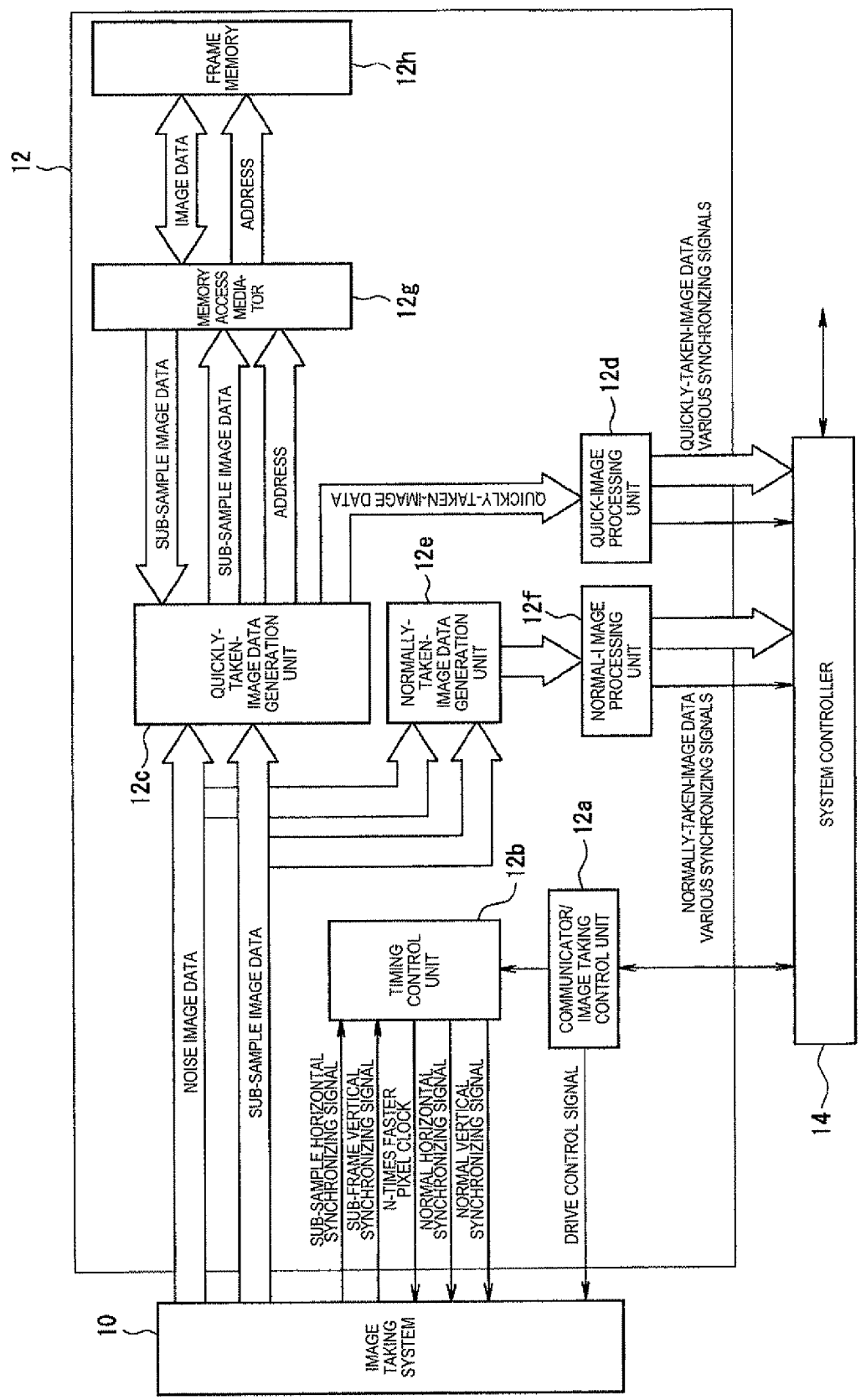
FIG. 7 is a block diagram showing an internal configuration of an image processing system 12.

Next, referring to FIG. 7, an internal configuration of the image processing system 12 will be described. FIG. 7 is a block diagram showing an internal configuration of the image processing system 12.

As shown in FIG. 7, the image processing system 12 includes a communicator/image taking control unit 12a, a timing control unit 12b, a quickly-taken-image data generation unit 12c, a quick-image processing unit 12d, a normally-taken-image data generation unit 12e, a normal-image processing unit 12f, a memory access mediator 12g, and a frame memory 12h.

The communicator/image taking control unit 12a receives a command from a system controller 20, generates a drive control signal in accordance with the received command, and transmits the drive control signal to the image taking system 10 and image processing system 12 so as to control operations of these systems. Specifically, the communicator/image taking control unit 12a controls various operations such as the start of image taking, the stop of image taking, a reset, and a hold.

The timing control unit 12b generates an N times faster pixel clock having a speed N times higher than the speed of a normal pixel clock and a normal horizontal synchronizing signal and a normal vertical synchronizing signal corresponding to the normal frame rate on the basis of a clock signal from a clock oscillator including a quartz vibrator and a ceramic oscillator, which are not shown, and transmits the generated pixel clock and synchronizing signals to the image taking system 10. Also, the timing control unit 12b receives a sub-sample horizontal synchronizing signal and a sub-frame vertical synchronizing signal from the image taking system 10 and generates various synchronizing signals and control signals used when performing internal processing.

The quickly-taken-image data generation unit 12c has a function of storing the first to N-th sub-sample image data and noise image data received from the image taking system 10 in the frame memory 12h via the memory access mediator 12g and a function of generating quickly-taken-image data (RAW image data) on the basis of the first to N-th sub-sample image data.

Specifically, in the process of storing sub-sample image data in the frame memory 12h, the addresses of each of the first to N-th sub-sample image data and noise image data are generated on the basis of a sub-frame vertical synchronizing signal and a sub-sample horizontal synchronizing signal from the timing control unit 12b, combinations of the generated addresses and the pieces of image data are made, and then the combinations are outputted to the memory access mediator 12g together with a write command.

Figure 8:
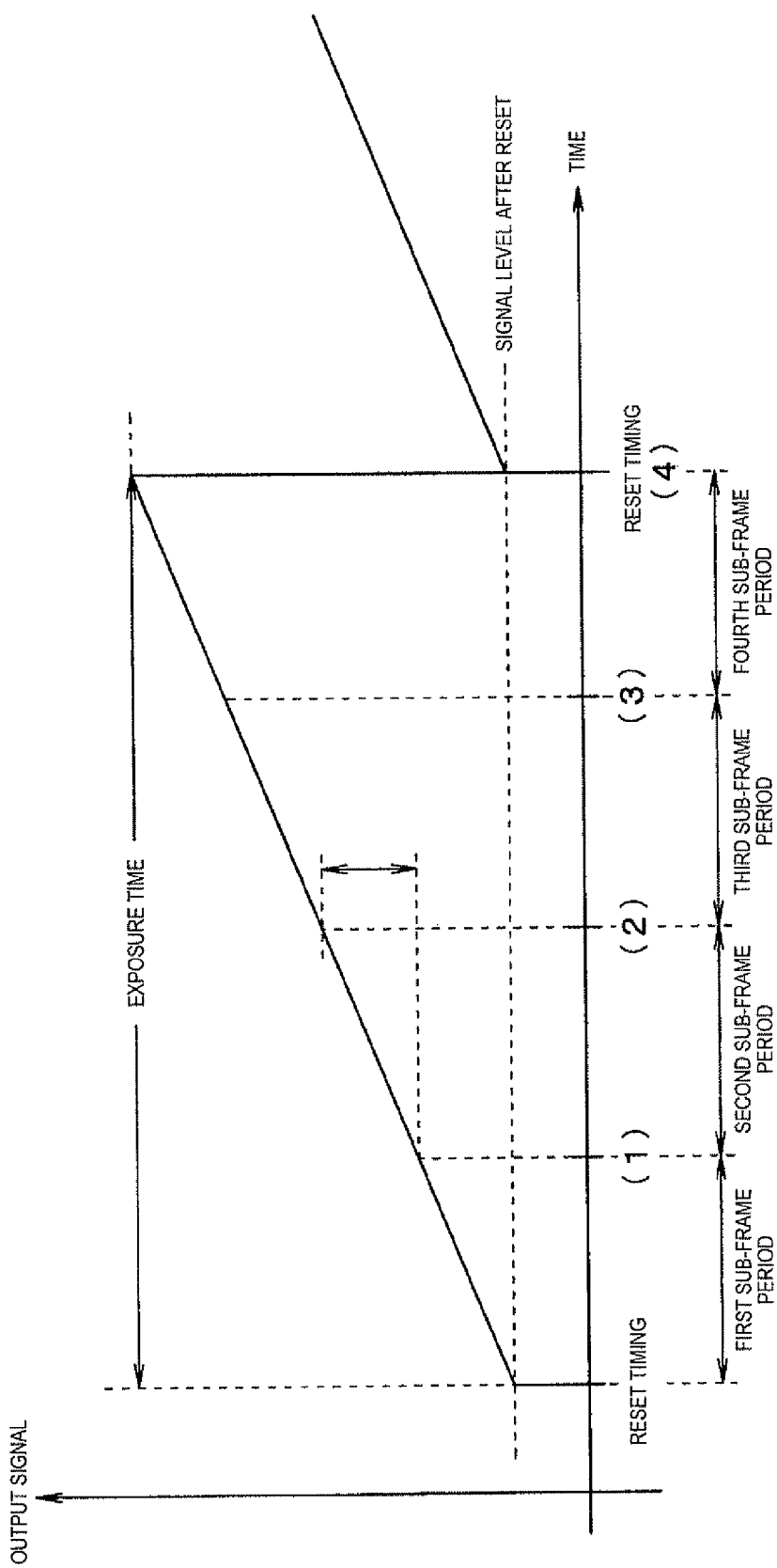
FIG. 8 is a graph showing an example of the movement of the amount of electric charge accumulated in a pixel.

Referring now to FIG. 8, a process of generating quickly-taken-image data will be described. FIG. 8 is a graph showing an example of the movement of the amount of electric charge accumulated on a pixel.

As shown in FIG. 8, a pixel signal is read out from each pixel of the sensor cell array 56 in a non-destructive manner at timings (1) to (4) shown in FIG. 8 during a period from immediately after a reset process to a subsequent reset process. Also, a reset process is performed immediately after a pixel signal is read out in a non-destructive manner at the timing (4). Therefore, electrical charge is accumulated on each pixel with the lapse of time so that the amount of accumulated electric charge is increased as shown by the slope of the signal output value in FIG. 8. Subsequently, when a reset process is performed, the signal output value is reduced to the after-reset signal level shown by a dotted line in FIG. 8. That is, the exposure time is determined by the timing at which a reset process is performed.

Therefore, electric charge components accumulated on each pixel due to the exposure in each sub-frame period are obtained from a difference between the amount of accumulated electric charge in each sub-frame period and the amount of accumulated electric charge in the preceding sub-frame.

Thus, the quickly-taken-image data generation unit 12c according to this embodiment performs a subtraction process on pieces of sub-sample image data corresponding to adjacent sub-frames using an internal subtracter (not shown) and generates first to N-th pieces of quickly-taken-image data corresponding to the sub-frame periods on the basis of the subtraction result.

As shown in FIG. 7, the quick-image processing unit 12d performs image processing, such as color interpolation, color conversion, noise removal, detail processing, and y correction, on the first to N-th pieces of quickly-taken-image data generated in the quickly-taken-image data generation unit 12c to generate color quickly-taken-image data that is final output data. Then, the quick-image processing unit 12d outputs the generated color quickly-taken-image data to the system controller 14 together with various synchronizing signals (horizontal synchronizing signal, vertical synchronizing signal, and pixel clock).

The normally-taken-image data generation unit 12e performs a subtraction process on the fourth sub-sample image data and noise image data using an internal subtracter (not shown) to generate normally-taken-image data on the basis of the subtraction result.

The normal-image processing unit 12f performs image processing such as color interpolation, color conversion, noise removal, detail processing, and y correction on the normally-taken-image data generated in the normally-taken-image data generation unit 12e to generate color normally-taken-image data that is final output data. Then, the normal-image processing unit 12f outputs the generated color normally-taken-image data to the system controller 14 together with various synchronizing signals (horizontal synchronizing signal, vertical synchronizing signal, and pixel clock).

The memory access mediator 12g accesses the frame memory 12h in accordance with a command for reading out or writing pixel data from or into the frame memory 12h from the quickly-taken-image data generation unit 12c.

When the memory access mediator 12g receives a command for writing pixel data from the quickly-taken-image data generation unit 12c, it outputs a request for writing pixel data to a specified address, to the frame memory 12h. On the other hand, when the memory access mediator 12g receives a command for reading out pixel data, it outputs a request for reading out pixel data from a specified address, to the frame memory 12h.

The frame memory 12h is a rewritable memory. Upon receipt of a request for reading out pixel data from the memory access mediator 12g, the frame memory 12h reads out sub-sample image data stored in an area having an address indicated by the request and passes the image data on to the memory access mediator 12g. On the other hand, upon receipt of a request for writing pixel data from the memory access mediator 12g, the frame memory 12h writes sub-sample image data received from the memory access mediator 12g in an area having an address indicated by the write request.

Figure 9:
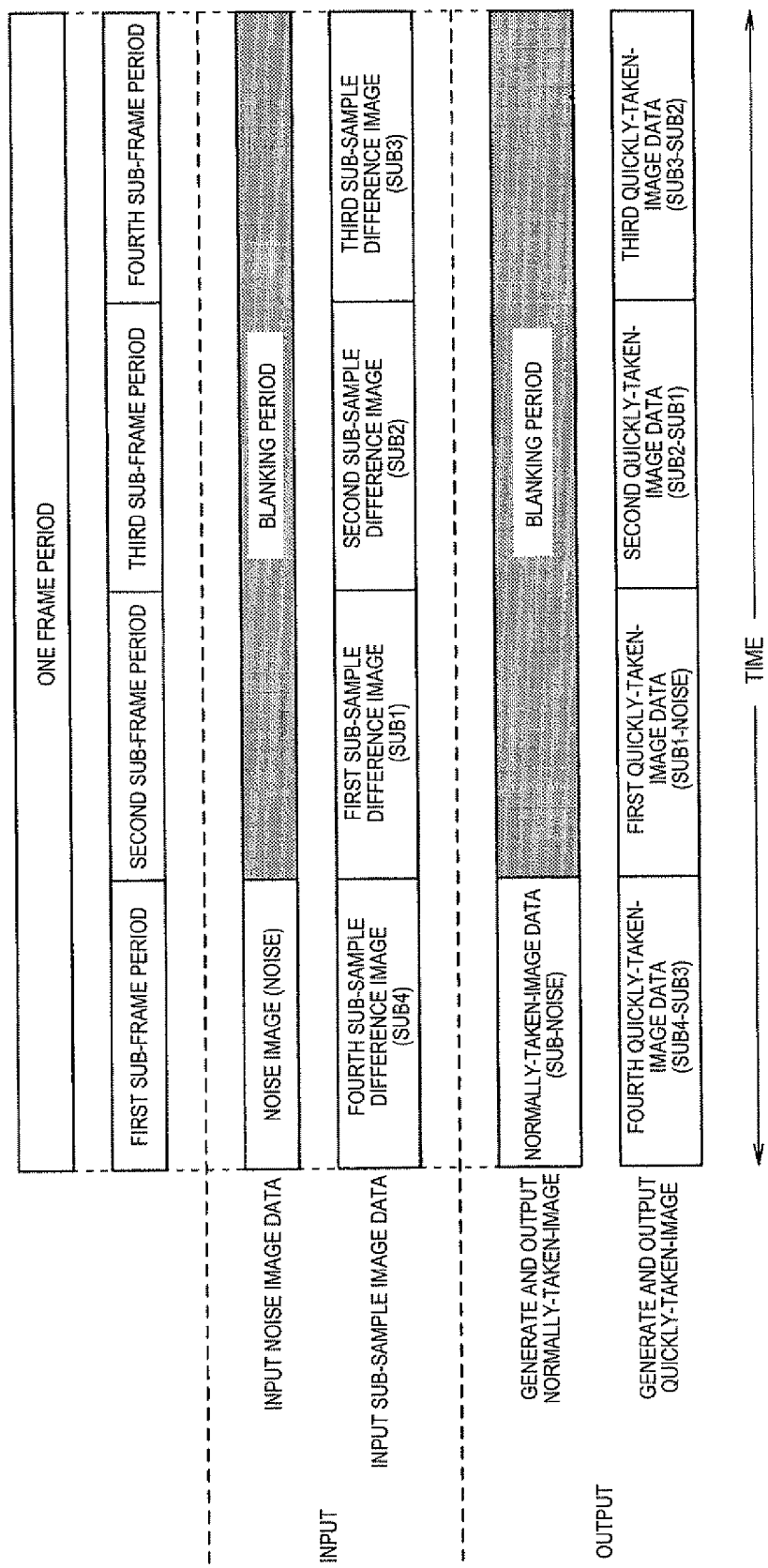
FIG. 9 is a diagram showing the timing at which image data is generated in each sub-frame period.

Referring now to FIG. 9, a method for generating image data in each of the quickly-taken-image data generation unit 12c and normally-taken-image data generation unit 12e will be described in detail. FIG. 9 is a diagram showing the timing at which image data is generated in each sub-frame period.

As shown in FIG. 9, in the first sub-frame period, the quickly-taken-image data generation unit 12c receives the fourth sub-sample image data from the image taking system 10 and reads out the third sub-sample image data from the frame memory 12h. Then, the quickly-taken-image data generation unit 12c performs a subtraction process on the values of pixels located in an identical position in the received fourth sub-sample image data and the read-out third sub-sample image data to and generates the fourth quickly-taken-image data from the subtraction result and outputs the generated fourth quickly-taken-image data to the quick-image processing unit 12d. That is, in the first sub-frame period, the quickly-taken-image data generation unit 12c generates fourth quickly-taken-image data with respect to the preceding sub-frame.

Simultaneously, in the first sub-frame period, the normally-taken-image data generation unit 12e performs a subtraction process on the values of pixels located in an identical position in the fourth sub-sample image data and noise image data received from the image taking system 10 and generates normally-taken-image data from the subtraction result and outputs the generated normally-taken-image data to the normal-image processing unit 12f. That is, in the first sub-frame period, the normally-taken-image data generation unit 12e generates normally-taken-image data with respect to the preceding frame.

Subsequently, in the second sub-frame period, the quickly-taken-image data generation unit 12c receives the first sub-sample image data from the image taking system 10 and reads out noise image data from the frame memory 12h. Then, the quickly-taken-image data generation unit 12c performs a subtraction process on the values (luminance values) of pixels located in an identical position in the received first sub-sample image data and read-out noise image data and generates first quickly-taken-image data from the subtraction result. Then, the quickly-taken-image data generation unit 12c outputs the generated first quickly-taken-image data to the quick-image processing unit 12d.

Subsequently, in the third sub-frame period, the quickly-taken-image data generation unit 12c receives the second sub-sample image data from the image taking system 10 and reads out the first sub-sample image data from the frame memory 12h. Then, the quickly-taken-image data generation unit 12c performs a subtraction process on the values of pixels located in an identical position in the received second sub-sample image data and the read-out first sub-sample image data and generates second quickly-taken-image data from the subtraction result. Then, the quickly-taken-image data generation unit 12c outputs the generated second quickly-taken-image data to the quick-image processing unit 12d. Likewise, in the fourth sub-frame period, the quickly-taken-image data generation unit 12c receives the third sub-sample image data from the image taking system 10 and reads out the second sub-sample image data from the frame memory 12h. Then, the quickly-taken-image data generation unit 12c performs a subtraction process on the values of pixels located in an identical position in the received second sub-sample image data and the read-out first sub-sample image data and generates third quickly-taken-image data from the subtraction result. Then, the quickly-taken-image data generation unit 12c outputs the generated third quickly-taken-image data to the quick-image processing unit 12d. Subsequently, the above-mentioned processes are repeated in the first sub-frame period and later sub-frames of a subsequent frame. These processes are repeatedly performed as long as images of the subject are being taken.

As shown in FIG. 2, the system controller 14 receives various commands from the information processing apparatus 400 via a transmission path (by wire or wirelessly). In accordance with these commands, the system controller 14 issues commands to the image taking system 10 and image processing system 12 so as to control operations of these systems.

Also, the system controller 14 receives normally-taken-image data and quickly-taken-image data from the image processing system 12 and accumulates these pieces of image data in the transmission frame memory 16 and then transmits the accumulated image data to the information processing apparatus 400 in conformity with the protocol of the transmission path.

The transmission frame memory 16 is a rewritable memory. Upon receipt of a request for reading out image data from the system controller 14, the transmission frame memory 16 reads out normally-taken-image data or quickly-taken-image data stored in an area having an address indicated by the request and then passes the read-out image data to the system controller 14. On the other hand, upon receipt of a request for writing image data from the system controller 14, the transmission frame memory 16 writes normally-taken-image data or quickly-taken-image data received from the system controller 14, in an area having an address indicated by the write request.

Next, referring now to FIGS. 10 to 12, operations actually performed by the state inspection system 1 according to this embodiment when the system is applied to the state inspection of agricultural products will be described.

Figure 10:
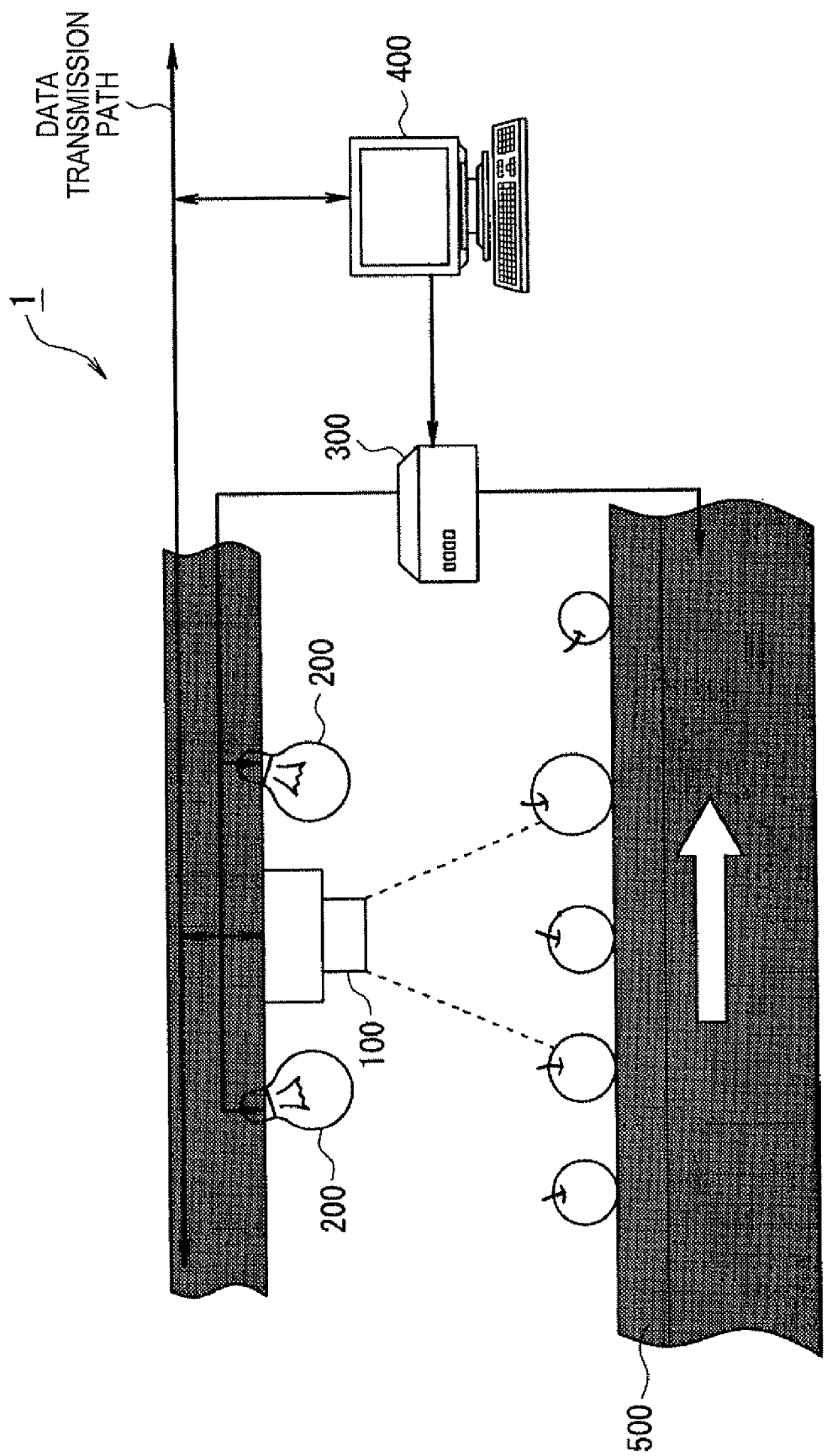
FIG. 10 is a drawing showing an example in which a state inspection system 1 is applied to the state inspection of agricultural products.
Figure 11:
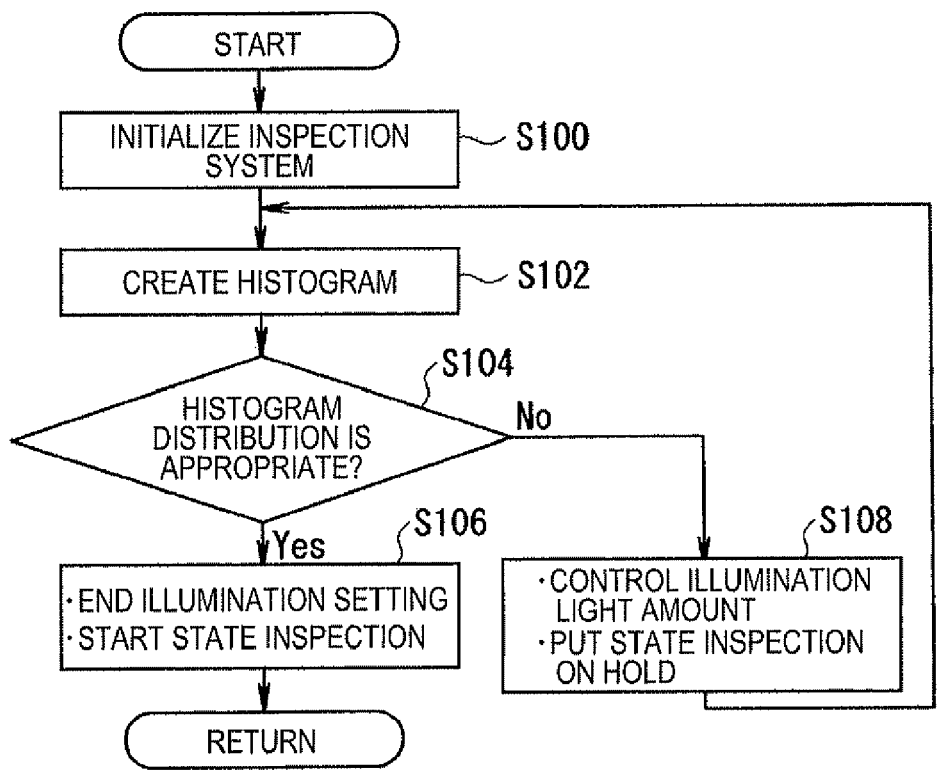
FIG. 11 is a flowchart showing the flow of a process performed by the state inspection system 1 before the system starts inspection.

FIG. 10 is a drawing showing an example in which the state inspection system 1 is applied to the state inspection of agricultural products (fruits, vegetables, etc.). FIG. 11 is a flowchart showing the flow of a process performed by the state inspection system 1 before the system starts the inspection. FIG. 12 is an example of a histogram of illumination information of normally-taken-image data.

The operations of the state inspection system 1 will be described assuming that the number N of times higher than the normal frame rate is four. When the state inspection system 1 according to this embodiment is applied to the state inspection of the agricultural products, the agricultural products are placed on the belt of the conveyor belt 500 and then moved. Also, the image taking apparatus 100 is disposed above the belt so that when the agricultural products moving with the agricultural products riding on the belt enters the image taking area, an image of the whole agricultural products will be taken. Also, the lighting system 200 is disposed so that the whole agricultural products moving in the image taking area of the image taking apparatus 100 will be lighted.

The lighting system 200, information processing apparatus 400, and conveyor belt 500 and are coupled to the control apparatus 300 via data transmission paths such as a LAN cable or a wireless LAN so that the former apparatuses and the latter apparatus exchange data with each other. The image taking apparatus 100 and information processing apparatus 400 are coupled to each other via a data transmission path so that these apparatuses exchange data with each other.

Hereafter, referring to FIGS. 11 and 12, operations performed by the state inspection system 1 when the system inspects the state of the agricultural products will be described.

When the components of the state inspection system 1 are powered on, the state inspection system 1 first performs an initialization operation (step S100).

The initialization operation is an operation performed prior to the state inspection of the agricultural products. First, the state inspection system 1 controls the amount of illumination light emitted by the lighting system 200. Specifically, the agricultural products are placed on the belt of the conveyor belt 500 and then the conveyor belt 500 is operated. Subsequently, the whole inspection subjects agricultural products) whose image is to be taken are put into the image taking area and then the operation of the conveyor belt 500 is stopped. In this state, images of the agricultural products located in the image taking area are taken so that normally-taken-image data and quickly-taken-image data is generated. When the initialization operation is performed, the image taking apparatus 100 transmits only the normally-taken-image data to the information processing apparatus 400 via a data transmission path.

Upon receipt of the normally-taken-image data of the inspection subjects from the image taking apparatus 100, the information processing apparatus 400 creates a histogram of luminance information on the basis of the normally-taken-image data (step S102). Then, the information processing apparatus 400 determines whether the luminance distribution in the histogram is appropriate (step S104).

Figure 12:
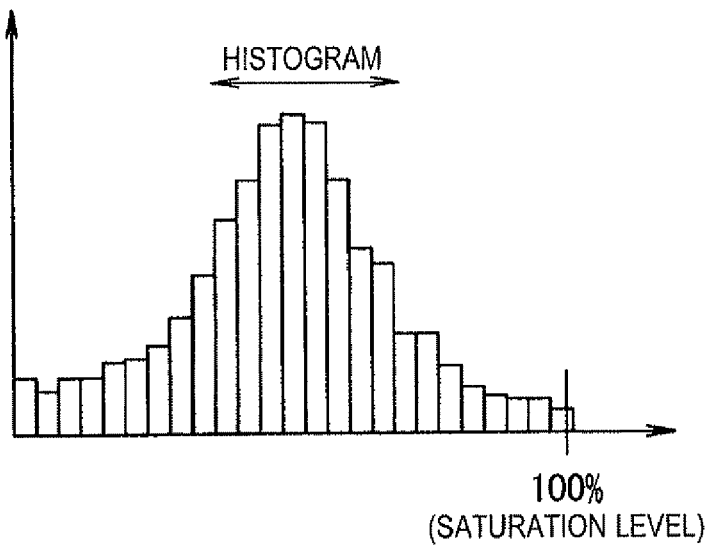
FIG. 12 is drawing showing an example of a histogram of luminance information of normally-taken-image data.

Specifically, if the luminance distribution in the created histogram is an appropriate luminance distribution like a histogram shown in FIG. 12 ("YES" in step S104), the information processing apparatus 400 ends the illumination setting. Thus, a series of processes for starting the state inspection are completed.

In contrast, if the luminance distribution in the created histogram is not appropriate ("NO" in step S104), the information processing apparatus 400 creates a command for changing the amount of illumination light and transmits the created command to the control apparatus 300 (step S108). Thus, the command for changing the amount of illumination light is transmitted to the lighting system 200 via the control apparatus 300 so that the amount of illumination light is changed.

For example, if the number of pixels that have reached the saturation level is large, the information processing apparatus 400 creates a command for reducing the amount of illumination light. In contrast, if the number of pixels having low luminance is large, the information processing apparatus 400 creates a command for increasing the amount of illumination light to the extent that the saturation level is not reached.

Each time the amount of illumination light emitted by the lighting system 200 is changed, an image of the inspection subjects is taken by the image taking apparatus 100. Then, a histogram is created from the obtained normally-taken-image data (step S102). Then, the information processing apparatus 400 determines whether the luminance distribution in the created histogram is appropriate (step S104).

In practice, an image of the inspection subjects moving while rising on the conveyor belt 500 is taken; therefore, an image of the inspection subjects that are moving may be taken and then the amount of illumination light may be controlled.

Also, on the basis of quickly-taken-image data obtained by taking an image of the inspection subjects that are moving, the information processing apparatus 400 determines whether the shapes of the inspection subjects are detected correctly. If the shapes are not detected correctly, for example, the information processing apparatus 400 generates a command for controlling the speed of the belt of the conveyor belt 500 and transmits the generated command to the controller 300. Thus, the speed of the belt of the conveyor belt 500 is changed.

For example, if the shapes are not recognized due to too high a belt speed, the information processing apparatus 400 generates a command for reducing the belt speed. However, in terms of inspection efficiency, it is preferable that the belt speed (transportation speed of the agricultural products) be high. Therefore, it is preferable to control the speed while trading off the image quality against the speed, so as to obtain the optimum speed.

After the above-mentioned initialization operation is completed, an operation start command is transmitted to the conveyor belt 500 so that the conveyor belt 500 starts operating. Thus, the inspection subjects placed on the belt starts moving and the state inspection of the inspection subjects is started.

Then, images of the inspection subjects passing through the image taking area are taken by the image taking apparatus 100. The obtained normally-taken-image data and first to fourth pieces of quickly-taken-image data are transmitted to the information processing apparatus 400 via a data transmission path.

The information processing apparatus 400 detects the colors or textures of the inspection subjects on the basis of the normally-taken-image data received from the image taking apparatus 100. For example, the information processing apparatus 400 performs pattern matching on the normally-taken-image data in consideration of color information so as to detect the colors or textures. For example, if the inspection subjects are apples, the range of the color (texture) is previously set on the basis of the luster, shading, or the like of the apples. The textures of the apples as the inspection subjects are determined (detected) on the basis of whether the colors in the normally-taken-image data fall within the set color range.

As described above, if the textures of the inspection subjects are determined on the basis of the normally-taken-image data adjusted so as to obtain an appropriate histogram, the states of the inspection subjects are determined accurately.

Also, each time the information processing apparatus 400 receives normally-taken-image data from the image taking apparatus 100, it creates a histogram of the luminance information of the image data and monitors whether there is an abnormality in the histogram. If an abnormality is found, the information processing apparatus 400 notifies the user of the fact and stops the state inspection process. Then, the information processing apparatus 400 controls the amount of illumination light so that the histogram will show an appropriate luminance distribution.

Also, the information processing apparatus 400 detects the shapes of the inspection subjects on the basis of the first to fourth pieces of quickly-taken-image data received from the image taking apparatus 100. For example, the information processing apparatus 400 binarizes each of the first to fourth pieces of quickly-taken-image data using a predetermined threshold and performs edge detection, area calculation, pattern matching, or the like on the basis of the resultant data to determine (detect) the shapes of the inspection subjects.

As described above, the shapes of the inspection subjects are determined on the basis of the first to fourth pieces of quickly-taken-image data obtained at a four-times faster frame rate. This allows increasing the belt speed compared with the related-art method, in which the shape is determined on the basis of normally-taken-image data.

Also, the information processing apparatus 400 generates sorting information according to the quality of the inspection subjects on the basis of the above-mentioned texture determination result and shape determination result and then transmits the generated sorting information to a sorting apparatus (not shown).

The sorting apparatus sorts out relevant inspection subjects on the basis of the sorting information from the information processing apparatus 400.

As is understood from the above description, the state inspection system 1 according to this embodiment is allowed to perform a reset process on each pixel in one frame period corresponding to the normal exposure time, as well as allowed to read out a pixel signal from each pixel of the sensor cell array 56 in a non-destructive manner at a frame rate N times higher than the normal frame rate in a normal one frame period.

This allows reading a pixel signal N times with the electrical charge accumulated on each pixel in one normal frame period.

Also, as described above, pixel signals are read out both at timings corresponding to the normal exposure times and timings corresponding to exposure times, each of which is shorter than the normal exposure time. This allows generating normally-taken-image data from pixel signals read out at timings corresponding to the normal exposure times, as well as allows generating the first to N-th pieces of quickly-taken-image data from pixel signals corresponding to the amounts of electric charge accumulated due to the exposure in each sub-frame period, which are obtained by obtaining a difference between pixel signals read out in temporally consecutive two sub-frame periods among the first to N-th sub-frame periods obtained by dividing one normal frame period into an N number of periods.

That is, in one normal frame period, image data corresponding to the normal exposure time and image data corresponding to the exposure time shorter than the normal exposure time is obtained simultaneously.

Also, the state inspection system 1 according to this embodiment is allowed to detect the textures of the inspection subjects on the basis of the normally-taken-image data, as well as allowed to detect the shapes or movements of the inspection subjects on the basis of the first to N-th pieces of quickly-taken-image data.

As a result, the textures of the inspection subjects are accurately detected and the shapes or movements of the moving inspection subjects are more accurately detected.

Also, the state inspection system 1 according to this embodiment is allowed to create a histogram of luminance information on the basis of the normally-taken-image data and to control the amount of illumination light of the lighting system so that the luminance distribution in the created histogram will be an appropriate distribution.

As a result, the amount of exposure of each pixel is controlled so that the exposure amount is an appropriate amount. Accordingly, a normally-taken-image of higher quality is obtained.

Also, pixel signals are read out immediately after a reset process and noise image data is generated from the read-out pixel signals. By using the generated noise image data, a fixed pattern noise component is eliminated from image data corresponding to the normal exposure time. As a result, normally-taken-image data of higher quality is obtained.

In the above-mentioned embodiment, the image taking system 10 corresponds to the image sensor according to the first aspect of the invention and the image taking apparatus 100 corresponds to the image taking apparatus according to the third aspect of the invention, and the state inspection system 1 corresponds to the state inspection system according to the fourth aspect of the invention.

In the above-mentioned embodiment, the function of performing a reset process on each pixel of the sensor cell array 56 of the image taking system 10 in the first sub-frame period corresponds to the reset processing unit according to the first aspect of the invention. Also, the function of reading out a pixel signal N times at a frame rate N times higher than the normal frame rate in each of the first to N-th sub-frame periods in the scanning line scanner 54 and sensor cell array 56 corresponds to the pixel signal readout unit according to the first aspect of the invention. Also, the quickly-taken-image data generation unit 12c and quick-image processing unit 12d correspond to the quickly-taken-image data generation unit according to the third aspect of the invention. Also, the standard image data generation unit 12e and standard image processing unit 12f correspond to the normally-taken-image data generation unit according to the third aspect of the invention.

Also, in the above-mentioned embodiment, the lighting system 200 corresponds to the lighting system according to the fourth aspect of the invention. Also, the function of controlling the amount of illumination light emitted by the lighting system 200 using the control apparatus 300 and information processing apparatus 400 corresponds to the light amount control unit according to the fourth aspect of the invention. Also, the information processing apparatus 400's function of detecting the texture of an inspection subject corresponds to the first detection unit according to the fourth aspect of the invention. Also, the information processing apparatus 400's function of detecting the shape of an inspection subject corresponds to the second detection unit according to the fourth aspect of the invention. Also, the information processing apparatus 400's function of creating a histogram corresponds to the histogram creation unit according to the fourth aspect of the invention.

In the above-mentioned embodiment, pixel signal data read out immediately after a reset process is transferred to the image processing system 12 via a channel different from a channel through which other pixel signal data is transferred, using the noise horizontal transfer unit 58a, but not limited thereto. Using the fact that noise image data is typically a fixed value without depending on light input, previously obtained noise image data may be stored in the frame memory 12h and the data may be used later. This allows realizing a similar process without having to provide the noise horizontal transfer unit 58a.

Also, in the above-mentioned embodiment, the number N of times higher than the normal frame rate used when a pixel signal is read out is set in a fixed manner like "N=4," but not limited thereto. The number of times of a frame rate may be set to an arbitrary number of times or may be variable. By adopting this configuration, if the shape or movement of an inspection subject is not successfully detected from quickly-taken-image data obtained using the current number of times, the number N of times is controlled so that appropriate quickly-taken-image data is obtained.

Also, in the above-mentioned embodiment, the information processing apparatus 400 creates a histogram of luminance information of normally-taken-image data and controls the amount of illumination light on the basis of the created histogram, but not limited thereto. A user that performs the inspection may give an instruction while visually inspecting an inspection subject displayed on a monitor, so that the light amount is controlled. In this case, if the information processing apparatus 400 determines that an unexpected variation has occurred in the histogram when performing an inspection operation, it may notify the user of the variation and urge the user to inspect the operation state of the state inspection system.

Also, in the above-mentioned embodiment, the information processing apparatus 400 binarizes the quickly-taken-image data and detects the shapes of the inspection subjects on the basis of the resultant data, but not limited thereto. The binarizing process may be performed by the image taking apparatus 100.

Also, in the above-mentioned embodiment, the state inspection system 1 is applied to the state inspection of the agricultural products (visual inspection), but not limited thereto. The state inspection system 1 may be applied to other types of inspection subjects such as non-living beings, e.g., mechanical parts, and an always moving object. Also, without being limited to a visual inspection, the state inspection system 1 may be used to detect the movement of an inspection subject from quickly-taken-image data and inspect the operation of the inspection subject during operation.

Also, in the above-mentioned embodiment, the amount of exposure of the image taking apparatus 100 is controlled by controlling the amount of illumination light emitted by the lighting system 200, but not limited thereto. For example, the exposure amount may be controlled using a function included in the image taking apparatus 100, such as controlling of the aperture amount of a mechanical aperture mechanism of the image taking apparatus 100. In this case, the image taking apparatus 100 corresponds to the image taking apparatus according to the second aspect of the invention.

The entire disclosure of Japanese Patent Application No: 2007-316863, filed Dec. 7, 2007 is expressly incorporated by reference herein.

What is claimed is:

1. An image sensor, comprising:
  a photoelectric conversion unit including a plurality of photoelectric conversion elements, the photoelectric conversion elements being disposed in a two-dimensional matrix, the photoelectric conversion elements converting received light into electric charge and accumulating the electric charge;
  a reset processing unit for performing a reset process, the reset process being a process of removing electric charge accumulated in each of the photoelectric conversion elements of the photoelectric conversion unit in a first sub-frame period among the first to N-th sub-frame periods, the N being a natural number of two or more, the first to N-th sub-frame periods being obtained by dividing each frame period of a frame rate corresponding to a normal exposure time into an N number of periods in the first to N-th order; and
  a pixel signal readout unit for reading out a pixel signal in a non-destructive manner, the pixel signal being an electric signal corresponding to an amount of electrical charge accumulated in each of the photoelectric conversion elements in each of the first to N-th sub-frame periods.

2. The image sensor according to claim 1, wherein
the pixel signal readout unit reads out the pixel signal from each of the photoelectric conversion elements immediately after the reset process.

3. An image taking apparatus, comprising
the image sensor according to claim 1, wherein
the image taking apparatus has a function of controlling an amount of exposure of each of the photoelectric conversion elements of the image sensor, and
the amount of exposure of each of the photoelectric conversion elements is controlled so that a pixel signal corresponding to an amount of electric charge accumulated during the normal exposure time, the pixel signal being read out by the pixel signal readout unit immediately before the reset process, does not reach a saturation level.

4. An image taking apparatus, comprising:
the image sensor according to claim 1;
a quickly-taken-image data generation unit for generating quickly-taken-image data corresponding to each of the first to N-th sub-frame periods based on a pixel signal corresponding to an amount of electric charge accumulated during each of the first to N-th sub-frame periods, the pixel signal being read out by the pixel signal readout unit of the image sensor; and
a normally-taken-image data generation unit for generating normally-taken-image data, the normally-taken-image data being image data corresponding to the normal exposure time, based on pixel signal data corresponding to an amount of electric charge accumulated during the first sub-frame period and a pixel signal corresponding to an amount of electric charge accumulated during the first to N-th sub-frame periods, the pixel signal data and the pixel signal both being read out by the pixel signal readout unit of the image sensor, wherein
the image taking apparatus has a function of controlling an amount of exposure of each of the photoelectric conversion elements of the image sensor.

5. The image taking apparatus according to claim 4, wherein
the pixel signal readout unit reads out a pixel signal from each of the photoelectric conversion elements immediately after a reset process,
the quickly-taken-image data generation unit generates the quickly-taken-image data corresponding to each of the first to N-th sub-frame periods based on a difference value between a luminance value of a first pixel signal and any one of a luminance value of a second pixel signal and a luminance value of a third pixel signal, the first pixel signal corresponding to an amount of electric charge accumulated during an n-th sub-frame period from the first sub-frame period, the n being a natural number of two or more and N or less, the second pixel signal corresponding to an amount of electric charge accumulated during an (n-1)-th sub-frame period from the first sub-frame period, the third pixel signal being read out immediately after the reset process, the first to third pixel signals being read out by the pixel signal readout unit, and
the normally-taken-image data generation unit generates the normally-taken-image data based on a difference value between a luminance value of a fourth pixel signal and a luminance value of a fifth pixel signal, the fourth pixel signal corresponding to an amount of electric charge accumulated during the first sub-frame period, the fifth pixel signal corresponding to an amount of electric charge accumulated during the first to N-th sub-frame periods, the fourth and fifth pixel signals being read out by the pixel signal readout unit.

6. The image taking apparatus according to claim 4, wherein
an amount of exposure of each of the photoelectric conversion elements is controlled so that a pixel signal corresponding to an amount of electric charge accumulated during the normal exposure time, the pixel signal being read out by the pixel signal readout unit immediately before the reset process, does not reach a saturation level.

7. A state inspection system for inspecting a state of an inspection subject moving in an inspection area, comprising:
the image taking apparatus according to claim 4;
a lighting system for lighting the inspection subject;
a light amount control unit for controlling a light amount of the lighting system based on normally-taken-image data obtained by taking an image of the inspection subject using the image taking apparatus;
a first detection unit for detecting information related to a texture of the inspection subject based on the normally-taken-image data; and
a second detection unit for detecting information related to any one of a shape and a movement of the inspection subject based on the quickly-taken-image data.

8. The state inspection system according to claim 7, further comprising
a histogram creation unit for creating a histogram of luminance information based on the normally-taken-image data obtained by taking an image of the inspection subject using the image taking apparatus, wherein
the light amount control unit controls the light amount of the lighting system based on the histogram created by the histogram creation unit.

* * * * *